(12) United States Patent
Gebauer et al.

(10) Patent No.: US 11,773,358 B2
(45) Date of Patent: Oct. 3, 2023

(54) METHOD FOR CONTROLLING CULTURE PARAMETERS IN A BIOREACTOR

(71) Applicant: Cytiva Sweden AB, Uppsala (SE)

(72) Inventors: Klaus Gebauer, Uppsala (SE); Eva Lindskog, Uppsala (SE); Lars Magnusson, Uppsala (SE)

(73) Assignee: Cytiva Sweden AB, Uppsala (SE)

(*) Notice: Subject to any disclaimer, the term of this patent is extended or adjusted under 35 U.S.C. 154(b) by 0 days.

(21) Appl. No.: 16/400,008

(22) Filed: Apr. 30, 2019

(65) Prior Publication Data

US 2019/0256812 A1 Aug. 22, 2019

Related U.S. Application Data

(63) Continuation-in-part of application No. 13/518,039, filed as application No. PCT/SE2010/051425 on Dec. 20, 2010, now abandoned.

(30) Foreign Application Priority Data

Dec. 22, 2009 (SE) .................................. 0951006-6

(51) Int. Cl.
  *C12M 1/00* (2006.01)
  *C12M 1/06* (2006.01)
  *C12M 1/36* (2006.01)

(52) U.S. Cl.
  CPC ............ *C12M 23/14* (2013.01); *C12M 27/02* (2013.01); *C12M 41/48* (2013.01)

(58) Field of Classification Search
  CPC .................................................... C12M 23/14
  USPC ...................................................... 435/286.1
  See application file for complete search history.

(56) References Cited

U.S. PATENT DOCUMENTS

| 6,029,101 | A | 2/2000 | Yoshida et al. |
| 6,673,008 | B1* | 1/2004 | Thompson ........... A01K 45/007 435/290.4 |
| 7,629,167 | B2 | 12/2009 | Hodge et al. |
| 8,506,886 | B2 | 8/2013 | Owen et al. |
| 2004/0214171 | A1 | 10/2004 | Sawada |
| 2004/0214271 | A1* | 10/2004 | Sawada ................. C12N 15/70 435/69.1 |
| 2005/0051723 | A1 | 3/2005 | Neagle et al. |

(Continued)

FOREIGN PATENT DOCUMENTS

| JP | 2003103169 A | 4/1991 |
| JP | H11119841 A | 4/1999 |

(Continued)

OTHER PUBLICATIONS

Enfors, S., et al., Bioprocess Technology—Fundamentals and Applications, Royal Institute of Technology, Jan. 2000, pp. 28-30.

(Continued)

*Primary Examiner* — Liban M Hassan
(74) *Attorney, Agent, or Firm* — Eversheds Sutherland (US) LLP

(57) ABSTRACT

A method for controlling at least one culture parameter in a bioreactor bag (1; 31 *a*, 31 *b*) provided in a bioreactor system, the method comprising the steps of:
providing bioreactor information to a control unit (5; 35) controlling the bioreactor system;
controlling the at least one culture parameter in dependence of the bioreactor information.

8 Claims, 3 Drawing Sheets

(56) References Cited

U.S. PATENT DOCUMENTS

| | | | |
|---|---|---|---|
| 2005/0112542 A1 | 5/2005 | West | |
| 2005/0158846 A1* | 7/2005 | Hibino | G06Q 10/06 |
| | | | 435/287.1 |
| 2005/0272146 A1 | 12/2005 | Hodge et al. | |
| 2005/0282269 A1 | 12/2005 | Proulx | |
| 2006/0019388 A1 | 1/2006 | Hutmacher et al. | |
| 2006/0110296 A1 | 5/2006 | Tajima et al. | |
| 2006/0216818 A1 | 9/2006 | Amano | |
| 2008/0254067 A1 | 10/2008 | Trepanier et al. | |
| 2009/0111179 A1* | 4/2009 | Hata | B01L 9/523 |
| | | | 435/394 |

FOREIGN PATENT DOCUMENTS

| | | | |
|---|---|---|---|
| JP | 2004299973 A | 10/1999 | |
| JP | 20040024179 A | 1/2004 | |
| JP | 2006288201 A | 10/2006 | |
| JP | 2008212049 A | 9/2008 | |
| JP | 2010530757 A | 9/2010 | |
| WO | 0210370 A1 | 2/2002 | |
| WO | 2009002772 A2 | 12/2008 | |
| WO | 2009042432 | 4/2009 | |

OTHER PUBLICATIONS

Wang Hongyu, et al., Chinese Medicinal Biotechnology vol. 4, No. 2, Apr. 30, 2009, pp. 158-159.

Japanese Notice of Opposition and Reasons for Revocation for Japanese Patent No. 6169847, dated Mar. 29, 2018, 39 pages (3 Pages of English Translation + 36 Pages Official Copy).

Pierce et al., Scatability of a Disposable Bioreactor from 25L-500L run in Perfusion Mode with a CHO-Based Cell Line: A Tech Review, BioProcessing Journal, vol. 3, No. 4, Jul./Aug. 2004, 9 pages.

GE Healthcare Bio-Sciences AB, "Wave Bioreactor System," Yeast Protocol, System 2/10, System 2/50, 2008, 6 pages.

GE Healthcare Bioscience BioProcess Corp., "Wave Disposable Technology," Aug. 2008, 32 pages.

Sppers et al., "Effects of Vessel Geometry, Fermenting Volume and Yeast Repitching on Fermenting Beer," J. Inst. Brew., 2009, 115(2):148-150.

European Office Action for EP Application No. 10839894.2, dated May 8, 2023 (27 pages).

\* cited by examiner

METHOD FOR CONTROLLING CULTURE PARAMETERS IN A BIOREACTOR

TECHNICAL FIELD OF THE INVENTION

The present invention relates to a method for controlling at least one culture parameter in a bioreactor bag provided in a bioreactor system. It further relates to a bioreactor system.

BACKGROUND OF THE INVENTION

In bioreactors culture parameters such as temperature, pH or DO are controlled by different means. For example the temperature can be controlled by a heater blanket surrounding the bioreactor, a heating/cooling element under the bioreactor, a liquid containing jacket surrounding the bioreactor, by heating/cooling the environment that surrounds the bioreactor, by heating/cooling coils in the bioreactor, and by controlling the temperature of liquid or gas that is added to the bioreactor. pH can be controlled by adding acid or base, by adding gases, or by culture medium renewal. DO can be controlled by e.g. adding oxygen and/or nitrogen to the bioreactor headspace, by adding oxygen and/or nitrogen into the bulk fluid, by changing the stirrer speed, by changing the rocking rate, by changing the rocking angle and by changing the vertical/horizontal movement of the bioreactor.

Control of temperature and/or pH and/or DO can be performed by using feed-back loops consisting of a) a measuring device such as a sensor or an electrode immersed into or in close proximity to the culture, b) a software for control and c) a means for affecting the respective parameter. The measuring device records the process value of the respective parameter and the sensor signal provides indata for the control software. The software adjusts the output of the controller means dependent on the current process value and the process history, the controller type and a unique set of controller parameters. The parameters can be accessible in the graphical user interface or hidden in the software.

SUMMARY

An object of the invention is to provide an improved method for controlling culture parameters in a bioreactor.

This is achieved in a method according to claim 1 and in a bioreactor system according to claim 9.

Hereby culture parameters in bioreactor bags of for example different size, at different weight or containing cell cultures at different status can be controlled differently.

Suitable embodiments are described in the dependent claims.

DETAILED DESCRIPTION OF THE EMBODIMENTS

According to the invention a bioreactor system is provided comprising at least one bioreactor bag comprising a culture fluid. A control unit of the system is arranged to receive information about the at least one bioreactor and to control at least one culture parameter in dependence of said bioreactor information. The bioreactor information could be for example the size of the bioreactor bag, the weight of the bioreactor bag including the contents of the bag or some information about the cell culture status in the bioreactor bag. The cell culture status information could for example be retrieved from a sensor provided in the cell culture in the bioreactor bag and the information could be for example the growth phase of the cell culture, information about the metabolites or information about the biomass. The controlling of at least one culture parameter could include the changing of PID parameters or suitably choosing between different sets of PID parameters in dependence of said bioreactor information. Hereby the controlling of the culture parameter can be automatically adapted for different bioreactor features, above called bioreactor information. If two bioreactor bags are provided into the same bioreactor system the culture parameters of the bioreactor bags can be independently controlled in dependence of the respective bioreactor information. More details of specific embodiments of the invention are given below.

Figure 1:
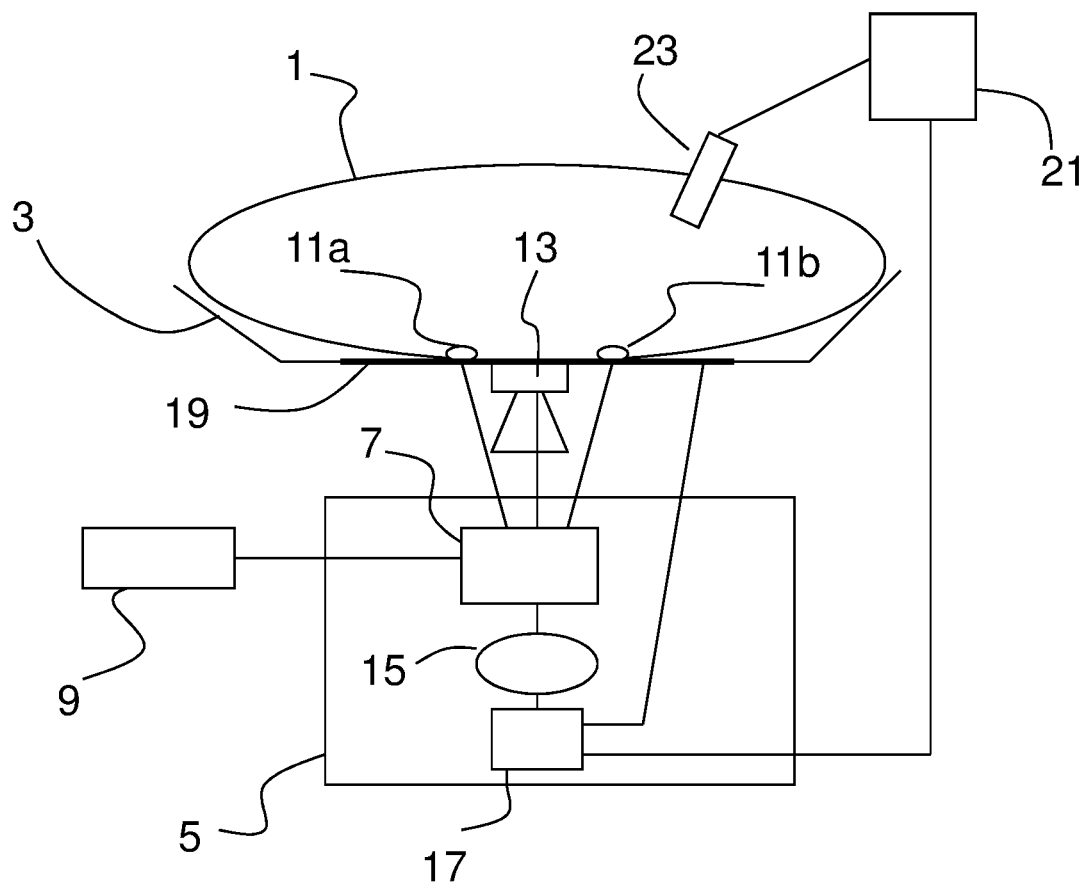
FIG. 1 is a schematic view of a bioreactor system according to one embodiment of the invention.

FIG. 1 is a schematic view of a bioreactor system according to one embodiment of the invention. In this embodiment a bioreactor bag 1 is provided in a rocking tray 3 (also called a support). The rocking motion is suitable for providing proper gassing and mixing of the culture fluid inside the bag 1. However other gassing and mixing methods could also be used such as horizontal and/or vertical movement, stirring with impellers, gas additions into the bioreactor headspace and/or into the bulk fluid and/or pumps. The bioreactor system comprises furthermore a control unit 5. The control unit 5 comprises a receiving means 7 that in this embodiment is connected to an input means 9. Via the input means 9 a user is adapted to provide information to the control means 5 about the size of the bioreactor bag 1. This input from the user could either be a manual input or some kind of automatic reading such as bar code reading or RF reading of an RFID tag. The receiving means 7 is furthermore suitably connected to at least one sensor in the bioreactor bag 1. In this embodiment the receiving means 7 is connected to two sensors 11a, 11b in the bioreactor bag 1. The sensors could be for example temperature sensors, pH sensors, DO sensors. The sensors 11a, 11b could also be sensors for measuring cell culture status, such as growth phase, biomass or metabolites. In this embodiment the receiving means 7 is further connected to a load cell 13 provided on the tray 3 under the bioreactor bag 1. Hereby the weight of the bioreactor bag with its contents of culture fluid will be received as an input to the receiving means 7 in the control unit 5 when the bioreactor bag is placed on the tray.

The control unit 5 comprises further a determining means 15 connected to the receiving means 7. In this embodiment the determining means 15 is adapted to use the information about the size of the bag, possibly together with information about at least one culture parameter received from the sensors 11a, 11b, to decide how to control this at least one culture parameter. In another embodiment information about the cell culture status from the sensors 11a, 11b is used to decide how to control the at least one culture parameter. In one embodiment of the invention there are predefined sets of parameters, possibly PID parameters, to use where each set is dedicated for each possible size (or in another embodiment: different possible cell culture states) of the bioreactor bag. In this case the determining means 15 only has to choose one of the sets of parameters depending of the size information received from the receiving means 7. In another embodiment of the invention more complicated functions for determining an optimal control of a culture parameter could be provided. The functions could for example be dependent on both size and shape of the bag, the size of the tray, the weight of the liquid content within the bag, culture parameter values received from the sensors 11*a*, 11*b* and/or cell culture state information received from the sensors 11*a*, 11*b*. Furthermore, according to one embodiment of the invention where a load cell 13 is provided, the determining means 15 could either use the size information or the weight of the bioreactor bag 1 for determining how to control the at least one culture parameter in the best way. A combination of the size information and the weight information could also be used.

The control unit 5 further comprises a controlling means 17 connected to the determining means 15 and adapted to control the at least one culture parameter according to what was determined in the determining means 15. In this embodiment the controlling means 17 is connected to a heating and/or cooling means 19 provided under the tray in the form of a heater pad/cooler pad. Other possible heating and/or cooling means could be heating or cooling of the surrounding gases, heating or cooling of the inlet gas to the bioreactor and heating and/or cooling means inside the bioreactor. According to the invention the heating and/or cooling means 19 will then control the temperature in the bioreactor bag 1 in dependence of the bioreactor information, which in this embodiment is bag size but could also be cell culture status or weight as described above. In this embodiment it is also shown that the controlling means 17 could be connected to some kind of adding means 21 connected to an inlet 23 to the bioreactor bag. This adding means 21 can be adapted to add for example one or more of oxygen, carbon dioxide, nitrogen, acid, base, specific nutrient concentrates or complete cell culture medium. Hereby other culture parameters than temperature can be controlled in dependence of the bioreactor information. These other culture parameters are for example pH, DO.

Since different bioreactor bag sizes can be used in the same bioreactor system this invention is very advantageous. When different bag sizes are used the culture parameters will change by different amounts when the same controlling will be applied. Heating a small bag size would for example be much faster than heating a large bag size. Hereby the adapted controlling according to the invention is advantageous and especially advantageous in bioreactor systems where the volume span is large.

A further advantage of the invention is that if two bioreactor bags are provided in the same tray the two bioreactor bags can be controlled independently and in dependence of each respective size or each respective other bioreactor information. Two bioreactor bags could be provided in the bioreactor system shown in FIG. 1.

Figure 2:
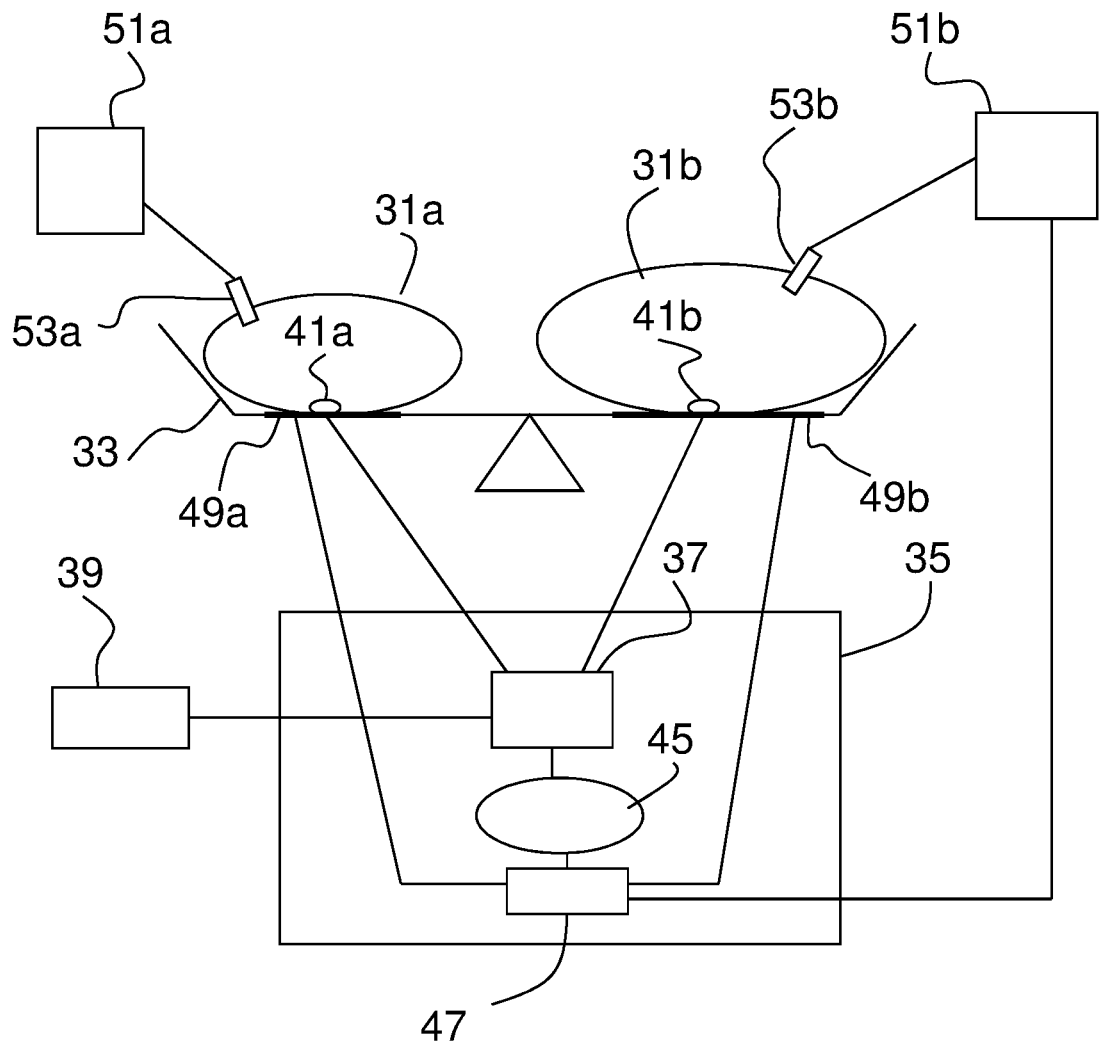
FIG. 2 is a schematic view of a bioreactor system according to another embodiment of the invention.

FIG. 2 shows schematically a bioreactor system according to the invention where two bioreactors 31*a*, 31*b* are provided in a rocking tray 33 (also called a support). A control unit 35 is provided in the bioreactor system. The control unit 35 comprises a receiving means 37 connected to an input means 39. Via the input means 39 a user is adapted to provide information to the control means 35 about the size of the two bioreactor bags 31*a*, 31*b*. This input from the user could either be a manual input or some kind of automatic reading such as bar code reading or RF reading of an RFID tag. The receiving means 37 is further suitably connected to at least one sensor 41*a*, 41*b* in each bioreactor bag 31*a*, 31*b*. The sensor could be for example a temperature sensor, pH sensor, DO sensor. The sensor could also possible measure cell culture status as defined above.

Similar to what was described in relation to FIG. 1 the control unit 35 comprises further a determining means 45 connected to the receiving means 37 and adapted to use the bioreactor information for example about the sizes of the bags suitably together with information about at least one culture parameter received from the sensors 41*a*, 41*b* to decide how to control this at least one culture parameter independently in each of the two bioreactor bags 31*a*, 31*b*. As described before there could be provided different sets of parameters adapted for different bag sizes and then the determining means has to choose an appropriate set of parameters for each bag.

Furthermore, the control unit 35 also comprises a controlling means 47 connected to the determining means 45. The controlling means 47 is also connected to for example a heating and/or cooling means 49*a*, 49*b* connected to each bioreactor bag 31*a*, 31*b* and/or an adding means 51*a*, 51*b* connected one to each bioreactor bag 31*a*, 31*b* through an inlet 53*a*, 53*b*. The controlling is the same as described above. The advantage is as described above that these two bioreactor bags can be controlled independently and in dependence of each respective bag size (or other bioreactor information).

Figure 3:
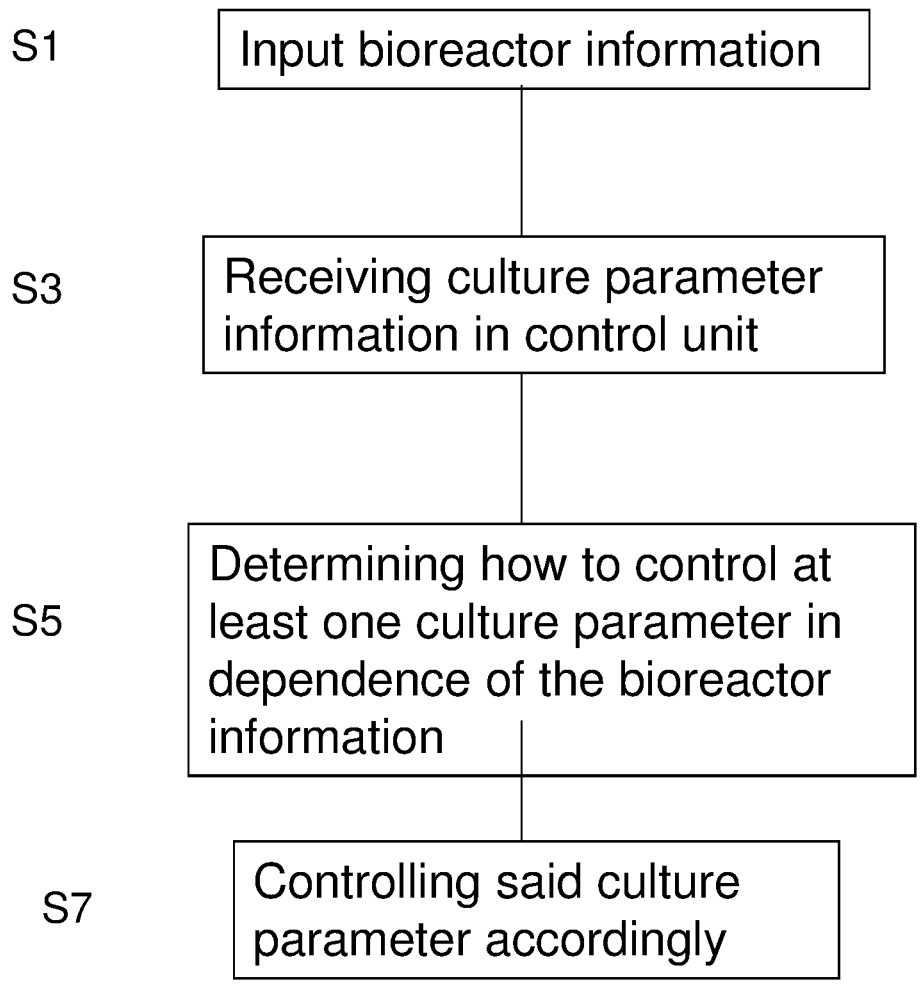
FIG. 3 is a flow chart of a method according to one embodiment of the invention.

FIG. 3 is a flow chart describing the method steps of one embodiment of the invention.

S1: Bioreactor information of one or two bags 1, 31*a*, 31*b* provided on the tray 3, 33 is provided to the control unit 5, 35 of the bioreactor system, possibly via the input means 9, 39. In one embodiment the bioreactor information is size and then the providing of information could be either manual input of bag size or some kind of bar code reading of the bag size or RF reading of an RFID tag provided on the bioreactor bags. In other embodiments the providing of bioreactor information to the control unit could be from sensors in the bioreactor bag or from a load cell on the tray as described above.

S3: Receiving culture parameter information in the control unit from sensors 11*a*, 11*b*, 41*a*, 41*b* provided in the bioreactor bags 1, 31*a*, 31*b*.

S5: Determining how to control at least one culture parameter in each bioreactor bag in dependence of each respective bioreactor information.

S7: Controlling said culture parameter accordingly.

The invention claimed is:

1. A method for controlling a culture in a bioreactor system, the method comprising:
 providing at least one bioreactor bag configured for holding a first culture fluid comprising the culture, wherein the bioreactor system comprises at least one sensor configured to generate first information related to at least one culture parameter, a support configured for mixing the first culture fluid inside the at least one bioreactor bag, and a control unit that is configured to communicate with the at least one sensor, further wherein:
 the at least one bioreactor bag is disposed on the support;
 the at least one sensor comprises a temperature sensor that is located inside of the at least one bioreactor bag; and
 the temperature sensor is connected to a receiving means, wherein the receiving means is in the control unit;
 receiving, using the control unit, the first information related to the at least one culture parameter, second information related to a size of the at least one bioreactor bag, and third information related to a weight of contents inside the at least one bioreactor bag;

determining, by the control unit, a plurality of predefined sets of control parameters that correspond to different sizes of bioreactors having different weights of contents inside the bioreactors, wherein each of the plurality of predefined sets of control parameters comprises a temperature parameter;

selecting, by the control unit, based on the first information, the second information, and the third information, a set of control parameters from the plurality of predefined sets of control parameters, wherein the selected set of control parameters corresponds to the size of the at least one bioreactor bag and the weight of contents inside the at least one bioreactor bag; and automatically implementing, by the control unit, a control procedure by setting the control parameters of the bioreactor system to the selected set of control parameters, so as to effect a change in the culture of the at least one bioreactor bag.

2. The method of claim 1, wherein the first information further includes a measurement selected from the group consisting of a pH measurement and a DO measurement.

3. The method of claim 1, wherein implementing the control procedure includes adjusting the at least one bioreactor bag to cause the at least one culture parameter to reach a predetermined value.

4. The method of claim 1, wherein the control unit is configured to receive the second information via one of a manual input, a barcode, and an RFID tag.

5. The method of claim 1, wherein the control unit is further configured to:

effect the change by performing one of heating the bioreactor bag, cooling the at least one bioreactor bag, adding oxygen to the at least one bioreactor bag, adding carbon dioxide to the at least one bioreactor bag, adding nitrogen to the at least one bioreactor bag, adding an acid to the at least one bioreactor bag, adding a base to the at least one bioreactor bag, and altering a gas flow in the at least one bioreactor bag.

6. The method of claim 1, further including selecting another predefined set of control parameters by the control unit.

7. The method of claim 6, wherein the at least one bioreactor bag further includes a second bioreactor bag, wherein the method further including controlling the second bioreactor bag according to the other set of specified control parameters.

8. The method of claim 1, further comprising:

providing a second bioreactor bag for holding a second culture fluid;

receiving, using the control unit, fourth information related to a size of the second bioreactor bag, and fifth information related to a weight of contents inside the second bioreactor bag; and independently controlling control parameters for the second bioreactor bag based at least in part on the fourth information and the fifth information.

\* \* \* \* \*